United States Patent [19]

Augelli-Szafran et al.

[11] Patent Number: 5,446,057
[45] Date of Patent: Aug. 29, 1995

[54] SUBSTITUTED TETRAHYDROPYRIDINE AND PIPERIDINE CARBOXYLIC ACIDS AS MUSCARINIC ANTAGONISTS

[75] Inventors: Corinne E. Augelli-Szafran, Ypsilanti; Juan C. Jaen, Plymouth; Roy Schwarz, Whitmore Lake; Anthony J. Thomas, Ann Arbor, all of Mich.

[73] Assignee: Warner-Lambert Company, Morris Plains, N.J.

[21] Appl. No.: 126,942

[22] Filed: Sep. 24, 1993

[51] Int. Cl.$^6$ .................. C07D 211/42; A61K 31/44
[52] U.S. Cl. .................. 514/356; 514/355; 546/315; 546/318; 546/322
[58] Field of Search .............. 546/315, 318, 322; 514/355, 356

[56] References Cited

U.S. PATENT DOCUMENTS

| | | | |
|---|---|---|---|
| 4,007,196 | 2/1977 | Christensen et al. | 546/197 |
| 4,745,123 | 5/1988 | Butler et al. | 514/356 |

FOREIGN PATENT DOCUMENTS

| | | | |
|---|---|---|---|
| 0219934 | 4/1987 | European Pat. Off. | 514/356 |

*Primary Examiner*—C. Warren Ivy
*Assistant Examiner*—Zinna N. Davis
*Attorney, Agent, or Firm*—Francis J. Tinney

[57] ABSTRACT

Substituted tetrahydropyridines and piperidinecarboxylic acids and derivatives thereof are described, as well as methods for the preparation and pharmaceutical composition of same, which muscarinic antagonists are useful as agents for inhibiting gastric acid release, for treating bradycardia, bronchoconstriction, urinary incontinence, atonic conditions of the gut and bladder, Parkinson's disease, dystonias, and Alzheimer's disease.

5 Claims, No Drawings

SUBSTITUTED TETRAHYDROPYRIDINE AND PIPERIDINE CARBOXYLIC ACIDS AS MUSCARINIC ANTAGONISTS

BACKGROUND OF THE INVENTION

The present invention relates to novel substituted tetrahydropyridine and piperidinecarboxylic acids and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are muscarinic antagonists.

The physiological actions of the neurotransmitter acetylcholine are mediated by two types of receptors, generally known by the terms 'nicotinic' and 'muscarinic'. Of particular interest are muscarinic cholinergic receptors, which mediate the effects of acetylcholine in the central as well as the peripheral nervous systems (CNS and PNS, respectively) [Taylor P., Brown J. H. in Basic Neurochemistry, 4th Edition; Siegel G., Agranoff B., Albers R. W., Molinoff P., Eds., Raven Press, New York: 1989:203–231]. Muscarinic receptors also play an important role in mediating the actions of acetylcholine on certain organs that are particularly responsive to cholinergic stimulation; for example, they affect the contractibility of smooth muscle in the gastrointestinal tract [Grider J. R., Bitar K. N., Makhlouf G. M., *Gastroenterology* 1987;93:951–957], the secretion of gastric acid [Kromer W., Gönne S., *Int. J. Exp. Clin. Pharmacol.* 1988;37(Suppl. 1):48–53], the force and rate of heart muscle contraction [Melchiorre C., Cassinelli A., et al., *Trends Pharm. Sci.* 1988;(Supplement):55], the secretory activity of exocrine glands that receive parasympathetic innervation, such as the salivary glands [Goyal R., *N. Engl. J. Med.* 1989;321:1022–1029], and the constriction of bronchial tissue [Maclagan J., Barnes P., *Trends Pharmacol. Sci.* 1989; (Suppl. "Subtypes of Muscarinic Receptors IV"):88–92], among others.

The existence of multiple muscarinic cholinergic receptor subtypes has been documented by functional, binding, and molecular biology studies. Initially, 3 muscarinic receptor subtypes ($M_1$, $M_2$, $M_3$) were characterized pharmacologically by the ability of certain synthetic ligands to recognize each receptor subtype with relative selectivity [Doods H. N., et al., *J. Pharmacol. Exp. Ther.* 1987;242:257–262; Levine R. R., Birdsall N. J. M., et al., *Trends Pharmacol. Sci.* 1989; (Suppl. "Subtypes of Muscarinic Receptors IV"):vii]. $M_1$ Receptors, found in the CNS and peripheral ganglia, are recognized with high affinity by the muscarinic antagonist pirenzepine. $M_2$ receptors, located primarily on cardiac cells, display high affinity towards the antagonists methoctramine and AF-DX 116; and $M_3$ receptors, found in smooth muscle and exocrine glands, are recognized with high affinity by the antagonists 4-DAMP (4-diphenylacetoxy-N-methylpiperidine methobromide) and hexahydrosiladifenidol.

At the molecular level, genes encoding 5 distinct muscarinic receptors have been cloned. The encoded receptor proteins have been termed m1, m2, m3, m4, and m5 [Bonner T. I., *Trends Pharmacol. Sci.* 1989; (Suppl. "Subtypes of Muscarinic Receptors IV"):11–15; Bonner T. I., Buckley N. J., Young A. E., Brann M. R., *Science* 1987;237:527–532; Hulme E. C., Birdsall N. J. M., Buckley N. J., *Ann. Rev. Pharmacol. Toxicol.* 1990;30:633–673]. These receptors possess different amino acid sequences and are selectively expressed throughout the body and in specific brain regions. mRNA for the m1 receptor has been found in the brain and exocrine glands; m2 mRNA is found in the heart, smooth muscle, and brain; m3 mRNA is detected in brain, glands, and smooth muscle; m4 and m5 mRNA are found primarily in the brain [Bonner T. I.; *T.I.N.S.* 1989;12:148–151]. The pharmacologically defined $M_1$, $M_2$, and $M_3$ receptors correspond quite closely to the molecularly defined m1, m2, and m3 receptors.

As indicated above, muscarinic receptors mediate the parasympathetic branch of the autonomic nervous system, which primarily controls gastric and intestinal tone and motility, gastric acid secretion, salivation, urination, lacrimation, cardiac, and ocular functions. Current and potential therapeutic applications of muscarinic antagonists include the treatment of peptic ulcers, irritable bowel syndrome, chronic obstructive airways disease, gastrointestinal, biliary, and urinary tract spasms, ophthalmic applications (as mydriatics and cycloplegics), reduction of excessive salivary or bronchial secretions during inhalation anesthesia, and the symptomatic treatment of parkinsonian movement disorders. The main limitations associated with the clinical use of available muscarinic antagonists stem from their relative lack of selectivity for the various muscarinic receptor subtypes. Thus, most muscarinic antagonists will produce many of the following side-effects in humans: cognitive impairment via blockade of brain muscarinic receptors, mydriasis, dry mouth, tachycardia, decreased sweating, blurred vision (by relaxation of the ciliary muscle), decreased gastrointestinal motility and constipation, etc. The lack of selectivity among these effects makes it difficult to address therapy in one specific indication.

Since individual therapeutic effects are associated with blockade of one or more specific muscarinic receptor subtypes, selective muscarinic antagonists with high specificity for the desired receptor subtypes would be very useful. These agents should provide the desired therapeutic benefit without the many unwanted side-effects of nonselective muscarinic antagonists. Currently available muscarinic antagonists can be classified into 3 main groups, based on their receptor subtype selectivity [Doods H. N., *Drug News Perspect.* 1992;5:345–352]: (1) agents such as pirenzepine, with the following type of receptor subtype selectivity: m1>m4>m3, m5, m2; (2) agents such as the cardiac-selective antagonist AF-DX 116: m2>m4, m1>m3, m5; and (3) what could be classified as non-m2 antagonists, exemplified by UH-AH 37: m1, m3, m4, m5>m2.

The following are just a few of the potential therapeutic uses of muscarinic antagonists with specific receptor subtype selectivities. Of course, nonselective antagonists might also be useful for these indications, but the side effects described above will limit their useful dosing range. In general, the molecular biology classification for the muscarinic receptor subtypes (m1, m2, m3, m4, m5) will be used, even though some of the agents' specificities may have been defined pharmacologically in the literature ($M_1$, $M_2$, M3).

Inhibition of Gastric Acid Release

Blockade of muscarinic receptors inhibits basal and stimulated gastric acid secretion, mainly by reducing volume secretion, an effect that is presumably mediated by m1 receptors. It has been clearly demonstrated that m1 antagonists possess utility in the treatment of peptic lesions, such as reflux esophagitis and gastric and duodenal ulcers [Stockbrugger R. W., *Meth. Find. Exp. Clin. Pharmacol.* 1989;11(Suppl. 1):79–86]. The effects of the relatively m1-selective antagonist pirenzepine, for example, have been extensively documented [Carmine A. A., Brogden R. N., *Drugs* 1985;30:85–126; Kromer W., Gönne S., *Int. J. Exp. Clin. Pharmacol.* 1988;37(Suppl. 1):48–53].

Antibradycardic Agents

Selective m2 muscarinic antagonists may be useful in the treatment of certain cardiovascular conditions, such as sinus bradycardia and bradycardic-hypotension syndrome after myocardial infarction. One of the best-known agents of this type is AF-DX 116, which is currently undergoing clinical evaluation as an antibradycardic drug [Doods H. N., Engel W., Su CAPF, Tanswell P., *Cardiovasc. Drug Rev.* 1991;9:30–40].

In a related application, m1 antagonists, such as pirenzepine, have been shown to improve exercise tolerance in patients with effort myocardial ischemia [Marraccini P., Orsini E., et al., *Am. J. Cardiol.* 1992;69:1407–1411].

Bronchodilators

Selective m1 antagonists may be useful in the treatment of those forms of asthma in which reflex mechanisms and/or increased cholinergic tone play a role, e.g., nocturnal asthma [Doods H. N., *Drug News Perspect.* 1992;5:345–352]. Mixed m1/m3 antagonists (e.g., DS-AH 14) have shown promise in the treatment of obstructive airway disease [Doods H. N., *Drug News Perspect.* 1992;5:345–352]. Also useful are muscarinic antagonists with the subtype selectivity profile m1>m3>m2, such as DAC 5889 [Doods H. N., *Drug News Perspect.* 1992;5:345–352]. Selective m3 antagonists have also been found to possess potential for the treatment of airway disease [Maclagan J., Barnes P., *Trends Pharm. Sci.* 1989; (Suppl. "Subtypes of Muscarinic Receptors IV"):88–92; Minette P. A., Barnes P. J., *Am. Rev. Respir. Dis.* 1990;141:S162–S165]. The muscarinic antagonist ipratropium bromide is used clinically as an inhalation bronchodilator.

In a related application, it is known that the parasympathetic nervous system regulates glandular secretion in the upper and lower respiratory tracts [Ishii T., *Pract. Otorhinolaryngol.* 1970;32:153–158]. Muscarinic m1 and m3 receptor subtypes regulate mucous secretion from human nasal mucosa, but m3 receptors may possess the predominant effects [Mullol J., Baraniuk J. N., et al., *J. Appl. Physiol.* 1992;73:2069–2073]. Mixed m1/m3 antagonists may be useful in allergic rhinitis, bronchial asthma, chronic bronchitis, etc.

Urinary Incontinence

Urinary incontinence can be the result of an overactive or unstable detrusor muscle. Muscarinic antagonists, exemplified by the agent oxybutynin, may play a role in the therapeutic treatment of the condition [Tonini M., et al., *J. Pharm. Pharmacol.* 1987;39:103–107]. Main limitations in the use of this agent include mydriasis, dry mouth, and some of the other typical anticholinergic side effects mentioned above. Muscarinic antagonists with some selectivity for m2 and/or m3 receptors have been suggested as potentially advantageous in the treatment of urinary incontinence [Kaiser C., Audia V. H., et al., *J. Med. Chem.* 1993;36:610–616].

CNS Uses of Muscarinic Antagonists

In the central nervous system (CNS), cholinergic neurotransmission is mediated primarily by muscarinic receptors. In hippocampus and regions of the cerebral cortex, they seem to be critical for higher cognitive processes such as memory and learning. In the striatum and motor cortex, they are involved in the control of movement. The collection of movement disorders typical of Parkinson's disease (tremor, rigidity, bradykinesis, etc.) results from a neurotransmitter imbalance in the basal ganglia, namely the loss of the inhibitory nigrostriatal dopaminergic circuitry which results in an excess of striatal acetylcholine. As a result, muscarinic antagonists are widely used in the early stages of Parkinson's disease [Fahn S., Caine D. B., *Neurology* 1978;28:5–7]. Muscarinic antagonists are also useful for the treatment of dystonias (e.g., torticollis) [Fahn S., *Neurology* 1983;33:1255–1261] and the parkinsonian movement disorders frequently associated with dopamine antagonist drug therapy (e.g., antiemetics and antipsychotics).

Alzheimer's disease is characterized by the progressive degeneration of cholinergic neurons that project from the basal forebrain to the cerebral cortex and hippocampus [Coyle J. T., Price D. L., DeLong M. R., *Science* 1983;219:1184–1190]. Cholinomimetic therapy (direct or indirect enhancement of the effects of endogenous acetylcholine) is currently viewed as the most promising short-term symptomatic treatment for the disease. Blockade of muscarinic m2 autoreceptors (located on cholinergic nerve terminals) is thought to stimulate the release of acetylcholine from cholinergic neurons [Raiteri M., Leardi R., Marchi M., *J. Pharmac. Exp. Ther.* 1984;228:209–214; Mash D. C., Potter L. T., *Neuroscience* 1986;19:551–564]. Thus, selective m2 antagonists might be useful as acetylcholine-releasing agents for the treatment of Alzheimer's disease and other dementias associated with cholinergic insufficiency.

Antispasmodics

Additionally, selective m3 muscarinic antagonists are useful as antispasmodics (treatment of atonic conditions of the gut and bladder [Mutschler E., Feifel R., et al., *Eur. J. Pharmacol.* 1990;183:117–119]. As such, they may find utility in conditions such as irritable bowel syndrome (IBS).

METHODOLOGY FOR THE DETERMINATION OF MUSCARINIC RECEPTOR SUBTYPE SELECTIVITY

As indicated above, conventional pharmacological classification of muscarinic receptor subtypes was based on the relative selectivity of certain muscarinic antagonists for the $M_1$, $M_2$, and $M_3$ receptors. Tissue preparations are frequently used for this type of work. However, the results are often clouded by the fact that most tissues express more than one muscarinic receptor subtype. Recently, each subtype of human muscarinic receptor has been stably cloned and expressed in Chinese hamster ovary (CHO) cells. These cell lines have been used to determine the relative affinity of novel muscarinic antagonists for each of the 5 cloned human muscarinic receptor subtypes [Buckley N. J., Bonner J. I., Buckley C. M., Brann M. R., *Mol. Pharmacol.* 1989;35:469–476; Dörje F., Wess J., et al., *J. Pharm. Exp. Ther.* 1991;256:727–733]. An additional advantage of these cloned cell lines is the ability to perform measures of functional activity directly on these cell cultures. Preferentially coupled to the stimulation of phosphoinositide metabolism via phospholipase C activation are m1, m3, and m5 receptors, while m2 and m4 receptors are coupled to the inhibition of adenylate cyclase [Peralta E. G., Ashkenazi A., et al., *Nature*

1988;334:434–437]. This knowledge allows the classification of compounds that bind to a specific receptor subtype as receptor agonists or antagonists. Using this technology, novel subtype-selective muscarinic antagonists have now been discovered and are the subject of this invention.

U.S. Pat. No. 4,745,123 ("'123") discloses a series of substituted 1,2,3,6-tetrahydro- and 1,2,5,6-tetrahydropyridine-3-carboxylic acids, esters, and amides possessing muscarinic binding activity and which are useful for the treatment of the symptoms of senile cognitive decline. However, unlike the compounds disclosed in the '123 patent, the compounds of the present invention are muscarinic antagonists and also possess marked selectivity for m1 and m4 muscarinic receptors over m2, m3, and m5, making them ideal agents in situations where selective blockade of m1 and/or m4 receptors is desired, e.g., gastric ulcers and Parkinson's disease, respectively.

SUMMARY OF THE INVENTION

Accordingly, the present invention is a compound of Formula I

                                                                I wherein
R is

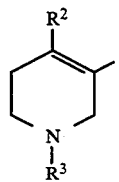

wherein
$R^2$ is
  alkyl of from 1 to 6 carbon atoms,
  alkenyl of from 2 to 10 carbon atoms,
  cycloalkyl of from 3 to 8 carbon atoms,
  aryl,
  aryl substituted by halogen, hydroxy, nitro, amino,

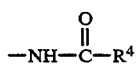

wherein
$R^4$ is
  alkyl of from 1 to 4 carbon atoms,
  alkyl of from 1 to 4 carbon atoms, or
  alkyloxy of from 1 to 4 carbon atoms, or,
  arylalkyl wherein the alkyl portion is from 1 to 3 carbon atoms and the aryl ring may be unsubstituted or substituted by halogen, hydroxy, nitro, amino,

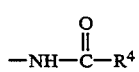

wherein
$R^4$ is
  alkyl of from 1 to 4 carbon atoms,
  alkyl of from 1 to 4 carbon atoms, or
  alkyloxy of from 1 to 4 carbon atoms,
  heteroaryl, or
  heteroaryl substituted by halogen, hydroxy, nitro, amino,

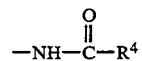

wherein
$R^4$ is
  alkyl of from 1 to 4 carbon atoms,
  alkyl of from 1 to 4 carbon atoms, or
  alkyloxy of from 1 to 4 carbon atoms, and
$R^3$ is alkyl of from 1 to 3 carbon atoms,

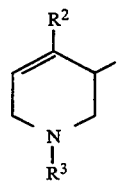

wherein
$R^2$ and $R^3$ are as defined above, or

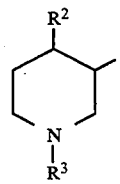

wherein
$R^2$ and $R^3$ are as defined above;
$R^1$ is —$XR^5$ wherein $R^5$ is
  alkyl of from 3 to 10 carbon atoms,
  alkenyl of from 2 to 10 carbon atoms,
  alkynyl of from 2 to 10 carbon atoms,
  cycloalkyl of from 3 to 8 carbon atoms,
  cycloalkylalkyl wherein alkyl is from 1 to 10 carbon atoms and cycloalkyl is as defined above,
  aryl,
  aryl substituted by halogen, hydroxy, nitro, amino,

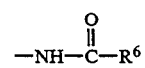

wherein
$R^6$ is
  alkyl of from 1 to 4 carbon atoms,
  alkyl of from 1 to 4 carbon atoms, or
  alkyloxy of from 1 to 4 carbon atoms,
  arylalkyl wherein alkyl is from 1 to 10 carbon atoms and the aryl ring may be unsubstituted or substituted by halogen, hydroxy, nitro, amino,

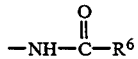

wherein $R^6$ is as defined above,
  alkyl of from 1 to 4 carbon atoms, or
  alkyloxy of from 1 to 4 carbon atoms,
  diarylalkyl wherein alkyl is from 1 to 10 carbons atoms, and the aryl ring is unsubstituted or substituted as defined above,
  arylalkenyl wherein alkenyl is from 2 to 10 carbon atoms and the aryl ring is unsubstituted or substituted as defined above,
  arylalkynyl wherein alkynyl is from 2 to 10 carbon atoms and the aryl ring is unsubstituted or substituted as defined above,

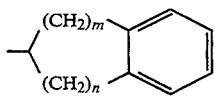

wherein
  m and n are each independently zero or an integer of 1 to 3, or

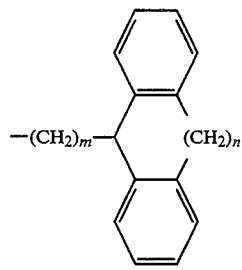

wherein
  m and n are as defined above; and
  X is O or S, or

wherein
  $R^7$ and $R^8$ are each independently
    hydrogen,
    alkyl of from 1 to 4 carbon atoms,
    cycloalkyl of from 3 to 8 carbon atoms,
    arylalkyl wherein the alkyl portion is from 1 to 6 carbon atoms and the aryl ring may be unsubstituted or substituted by halogen, hydroxy, nitro, amino,

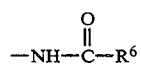

wherein
  $R^6$ is as defined above,
  alkyl of from 1 to 4 carbon atoms, or
  alkyloxy of from 1 to 4 carbon atoms, or
  $R^7$ and $R^8$ when taken together with the nitrogen atom to which they are attached form a pyrrolidinyl, piperidinyl, 4-(diphenylmethylene)piperidinyl, 4-alkylpiperazinyl wherein alkyl is from 1 to 6 carbon atoms, piperazinyl, azepinyl, morpholinyl, thiomorpholinyl, or isoxazolyl ring; or a pharmaceutically acceptable salt thereof with the proviso that when R is

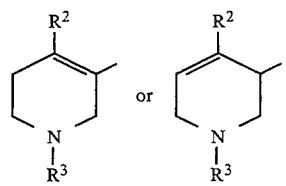

wherein
  $R^2$ and $R^3$ are as defined above
and
  $R^1$ is $OR^5$
  $R^5$ is not
    alkyl of from 3 to 5 carbon atoms,
    alkenyl of from 2 to 5 carbon atoms,
    cycloalkyl of from 3 to 5 carbon atoms,
    phenyl,
    phenyl substituted by halogen, hydroxy, nitro, amino,

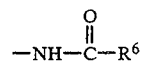

wherein
  $R^6$ is
    alkyl of from 1 to 4 carbon atoms,
    alkyl of from 1 to 4 carbon atoms,
    alkyloxy of from 1 to 4 carbon atoms, or
    phenylalkyl wherein alkyl is from 4 to 6 carbon atoms and the phenyl ring may be unsubstituted or substituted by halogen, hydroxy,
    alkyl of from 1 to 6 carbon atoms, or
    alkyloxy of from 1 to 4 carbon atoms, and with the further proviso that when R is

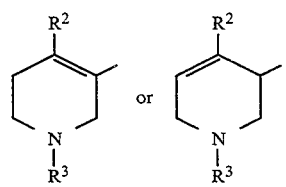

wherein
  $R^2$ and $R^3$ are as defined above
and
  $R^1$ is

$R^7$ and $R^8$ are not each independently
    hydrogen,
    alkyl of from 1 to 4 carbon atoms,
    cycloalkyl of from 3 to 8 carbon atoms,
    phenylalkyl wherein the alkyl portion is from 1 to 6 carbon atoms and the phenyl ring may be unsubstituted or substituted by halogen, hydroxy,
    alkyl of from 1 to 6 carbon atoms,
    alkyloxy of from 1 to 4 carbon atoms, or
  $R^7$ and $R^8$ when taken together with the nitrogen atom to which they are attached form a pyrrolidinyl, piperidinyl, 4-(diphenylmethylene)piperidinyl, 4-alkylpiperazinyl wherein alkyl is from 1 to 6 carbon atoms, piperazinyl, azepinyl, morpholinyl, thiomorpholinyl, or isoxazolyl ring.

As muscarinic antagonists, the compounds of Formula I are useful as inhibitors of gastric acid release, as antibradycardiac agents, as bronchodilators, as agents for the treatment of urinary incontinence, and as antispasmodic agents. They are also useful as central nervous system agents in the treatment of Parkinson's disease, the treatment of dystonias, and in the treatment of Alzheimer's disease.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like. The term "alkenyl" means a straight or branched unsaturated hydrocarbon radical having from 2 to 10 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, and the like.

The term "alkynyl" means a straight or branched triple bonded unsaturated hydrocarbon radical having from 2 to 10 carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, and the like.

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "cycloalkylalkyl" means a cycloalkyl group as defined above attached to an alkyl group as defined above and includes, for example, cyclopropylmethyl, cyclohexylmethyl, and the like.

The term "alkyloxy" means alkyl-O- of from 1 to 10 carbon atoms as defined above for "alkyl."

The term "aryl" means an aromatic radical which is a phenyl group, a phenyl group substituted by 1 to 4 substituents selected from alkyl as defined above, alkyloxy as defined above, halogen, hydroxy, nitro, amino, or

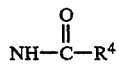

wherein $R^4$ is alkyl, a naphthyl group, or a naphthyl group substituted by 1 to 4 substituents selected from alkyl as defined above, alkyloxy as defined above, halogen, hydroxy, nitro, amino, or

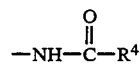

wherein $R^4$ is alkyl

The term "arylalkyl" means an aromatic radical, as defined above, attached to an alkyl group as defined above.

The term "diarylalkyl" means 2 aromatic radicals, as defined above, attached to the same or different carbon atoms of an alkyl group as defined above.

The term "arylalkenyl" means an aromatic radical, as defined above, attached to an alkenyl group as defined above.

The term "arylalkynyl" means an aromatic radical, as defined above, attached to an alkynyl group as defined above.

The term "phenylalkyl" means a phenyl radical attached to an alkyl group as defined above.

The term "heteroaryl" means a heteroaromatic radical which is 2-, 3-, or 4-pyridinyl or 2-, 3-, or 4-pyridinyl substituted by alkyl, alkyloxy, or halogen, 2-, 4-, or 5-pyrimidinyl or 2-, 4-, or 5-pyrimidinyl substituted by alkyl, alkyloxy, or halogen, 2-pyrazinyl or 2-pyrazinyl substituted by alkyl, alkyloxy, or halogen, 2- or 3-thienyl or 2- or 3-thienyl substituted by alkyl or halogen, 2- or 3-furanyl or 2- or 3-furanyl substituted by alkyl or halogen, 2-, 4-, or 5-thiazolyl or 2-, 4-, or 5-thiazolyl substituted by alkyl or halogen.

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group 11A of the periodic table and includes, for example, calcium, barium, strontium, magnesium, and the like.

"Noble metal" is platinum, palladium, rhodium, ruthenium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic monoand dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate [see, for example, Berge S. M., et al., "Pharmaceutical Salts," *Journal of Pharmaceutical Science* 1977;66:1–19].

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention may exist as a mixture of cis and trans isomers or as the individual cis and trans isomers. The mixture of isomers as well as the individual isomers are intended to be encompassed within the scope of the present invention. Additionally, certain of the compounds of the present invention possess one or more chiral centers and each center may exist in the R or S configuration. The present invention includes all enantiomeric and epimeric forms as well as the appropriate mixtures and racemates thereof.

A preferred compound of Formula I is one wherein R is

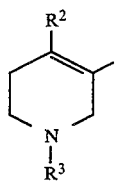

wherein
R$^2$ is
  cycloalkyl of 6 carbon atoms,
  phenyl, or
  phenyl substituted by halogen, hydroxy, nitro, amino,

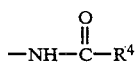

wherein
R$^4$ is
  alkyl of from 1 to 4 carbon atoms,
  alkyl of from 1 to 4 carbon atoms, or
  alkyloxy of from 1 to 4 carbon atoms, and
R$^3$ is alkyl of from 1 to 3 carbon atoms,

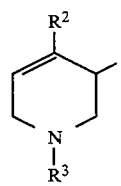

wherein
R$^2$ and R$^3$ are as defined above, or

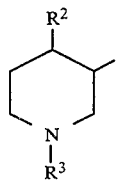

wherein
R$^2$ and R$^3$ are as defined above;
R$^1$ is XR$^5$ where R$^5$ is
  alkyl of from 7 to 10 carbon atoms,
  alkenyl of from 7 to 10 carbon atoms,
  alkynyl of from 3 to 7 carbon atoms,
  cycloalkyol of from 5 to 6 carbon atoms,
  cycloalkylalkyl wherein alkyl is from 1 to 3 carbon atoms and cycloalkyl is as defined above,
  arylalkyl wherein alkyl is from 7 to 8 carbon atoms and the aryl ring may be unsubstituted or substituted by halogen, hydroxy, nitro, amino,

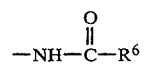

wherein
R$^6$ is as defined above,
  alkyl of from 1 to 4 carbon atoms, or
  alkyloxy of from 1 to 4 carbon atoms,
  diarylalkyl wherein alkyl is from 1 to 5 carbon atoms and the aryl ring is unsubstituted or substituted as defined above,
  arylalkenyl wherein alkenyl is from 3 to 10 carbon atoms and the aryl ring is unsubstituted or substituted as defined above, or
  arylalkynyl wherein alkynyl is from 3 to 10 carbon atoms and the aryl ring is unsubstituted or substituted as defined above; and
X is O.

A more preferred compound of Formula I is one wherein
R is

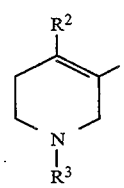

wherein
R$^2$ is
  cycloalkyl of 6 carbon atoms,
  phenyl,
  phenyl substituted by halogen, alkyl of from 1 to 3 carbon atoms, or alkyloxy of from 1 to 3 carbon atoms, and
R$^3$ is alkyl of from 1 to 3 carbon atoms,

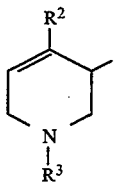

wherein
R² and R³ are as defined above, or

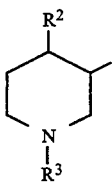

wherein
R² and R³ are as defined above;
R¹ is XR⁵ wherein R⁵ is
  alkyl of from 7 to 10 carbon atoms,
  alkenyl of from 7 to 10 carbon atoms,
  alkynyl of from 3 to 7 carbon atoms,
  cycloalkyl of 6 carbon atoms,
  cycloalkylalkyl wherein alkyl is from 1 to 3 carbon atoms and cycloalkyl is as defined above,
  arylalkyl wherein alkyl is from 7 to 8 carbon atoms and the aryl ring is unsubstituted or substituted by halogen, nitro, alkyl of from 1 to 3 carbon atoms, or alkyloxy of from 1 to 3 carbon atoms,
  diarylalkyl wherein alkyl is from 1 to 5 carbon atoms and the aryl ring is unsubstituted or substituted by halogen, nitro, alkyl of from 1 to 3 carbon atoms, or alkyloxy of from 1 to 3 carbon atoms,
  arylalkenyl wherein alkenyl is from 3 to 7 carbon atoms and the aryl ring is unsubstituted or substituted by halogen, nitro, alkyl of from 1 to 3 carbon atoms, or alkyloxy of from 1 to 3 carbon atoms; and
X is O.

Particularly valuable are:
1-Ethyl-1,2,5,6-tetrahydro-4-phenyl-3-pyridinecarboxylic acid, 3-cyclohexylpropyl ester;
1-Ethyl-1,2,3,6-tetrahydro-4-phenyl-3-pyridinecarboxylic acid, 3-cyclohexylpropyl ester;
1-Ethyl-1,2,5,6-tetrahydro-4-phenyl-3-pyridinecarboxylic acid, 2-cyclohexylethyl ester;
1-Ethyl-1,2,3,6-tetrahydro-4-phenyl-3-pyridinecarboxylic acid, 2-cyclohexylethyl ester;
1-Ethyl-1,2,5,6-tetrahydro-4-phenyl-3-pyridinecarboxylic acid, 2,2-diphenylethyl ester;
1-Ethyl-1,2,3,6-tetrahydro-4-phenyl-3-pyridinecarboxylic acid, 2,2-diphenylethyl ester;
1-Ethyl-1,2,5,6-tetrahydro-4-phenyl-3-pyridinecarboxylic acid, cyclohexylmethyl ester;
1-Ethyl-1,2,3,6-tetrahydro-4-phenyl-3-pyridinecarboxylic, cyclohexylmethyl ester;
1-Ethyl-1,2,5,6-tetrahydro-4-phenyl-3-pyridinecarboxylic acid, 1-naphthyl ester;
1-Ethyl-1,2,3,6-tetrahydro-4-phenyl-3-pyridinecarboxylic, 1-naphthyl ester;
1-Ethyl-1,2,5,6-tetrahydro-4-phenyl-3-pyridinecarboxylic acid, diphenylmethyl ester;
1-Ethyl-1,2,3,6-tetrahydro-4-phenyl-3-pyridinecarboxylic, diphenylmethyl ester;
1-Ethyl-1,2,5,6-tetrahydro-4-phenyl-3-pyridinecarboxylic acid, 2,3-dihydro-1H-inden-1-yl ester;
1-Ethyl-1,2,3,6-tetrahydro-4-phenyl-3-pyridinecarboxylic acid, 2,3-dihydro-1H-inden-1-yl ester;
1-Ethyl-1,2,5,6-tetrahydro-4-phenyl-3-pyridinecarboxylic acid, 1,2,3,4-tetrahydro-1-naphthalenyl ester;
1-Ethyl-1,2,3,6-tetrahydro-4-phenyl-3-pyridinecarboxylic acid, 1,2,3,4-tetrahydro-1-naphthalenyl ester;
1-Ethyl-1,2,5,6-tetrahydro-4-phenyl-3-pyridinecarboxylic acid, 3,3-diphenylpropyl ester;
1-Ethyl-1,2,3,6-tetrahydro-4-phenyl-3-pyridinecarboxylic acid, 3,3-diphenylpropyl ester;
1-Ethyl-1,2,5,6-tetrahydro-4-phenyl-3-pyridinecarboxylic acid, (tetrahydro-2-furanyl)methyl ester;
1-Ethyl-1,2,3,6-tetrahydro-4-phenyl-3-pyridinecarboxylic acid, (tetrahydro-2-furanyl)methyl ester;
1-Ethyl-1,2,5,6-tetrahydro-4-cyclohexyl-3-pyridinecarboxylic acid, 4-phenylbutyl ester;
1-Ethyl-1,2,3,6-tetrahydro-4-cyclohexyl-3-pyridinecarboxylic acid, 4-phenylbutyl ester;
1-Ethyl-1,2,5,6-tetrahydro-4-cyclohexyl-3-pyridinecarboxylic acid, hexyl ester;
1-Ethyl-1,2,3,6-tetrahydro-4-cyclohexyl-3-pyridinecarboxylic acid, hexyl ester;
1-Ethyl-1,2,5,6-tetrahydro-4-cyclohexyl-3-pyridinecarboxylic acid, 2-phenylethyl ester;
1-Ethyl-1,2,3,6-tetrahydro-4-cyclohexyl-3-pyridinecarboxylic acid, 2-phenylethyl ester;
1-Ethyl-1,2,5,6-tetrahydro-4-cyclohexyl-3-pyridinecarboxylic acid, cyclohexyl ester;
1-Ethyl-1,2,3,6-tetrahydro-4-cyclohexyl-3-pyridinecarboxylic acid, cyclohexyl ester;
1-Ethyl-1,2,5,6-tetrahydro-4-cyclohexyl-3-pyridinecarboxylic acid, n-octyl ester;
1-Ethyl-1,2,5,6-tetrahydro-4-cyclohexyl-3-pyridinecarboxylic acid, n-nonyl ester;
1-Ethyl-1,2,5,6-tetrahydro-4-cyclohexyl-3-pyridinecarboxylic acid, n-heptyl ester;
1-Ethyl-1,2,3,6-tetrahydro-4-cyclohexyl-3-pyridinecarboxylic acid, n-octyl ester;
1-Ethyl-1,2,3,6-tetrahydro-4-cyclohexyl-3-pyridinecarboxylic acid, n-nonyl ester;
1-Ethyl-1,2,5,6-tetrahydro-4-cyclohexyl-3-pyridinecarboxylic acid, 2-cyclohexylethyl ester;
1-Ethyl-1,2,3,6-tetrahydro-4-cyclohexyl-3-pyridinecarboxylic acid, 2-cyclohexylethyl ester;
1-Ethyl-1,2,5,6-tetrahydro-4-cyclohexyl-3-pyridinecarboxylic acid, 2,2-diphenylethyl ester; and
1-Ethyl-1,2,3,6-tetrahydro-4-cyclohexyl-3-pyridinecarboxylic acid, 2,2-diphenylethyl ester;
or a pharmaceutically acceptable salt thereof.

The compounds of Formula I are valuable muscarinic antagonists. The test employed indicates that compounds of Formula I possess muscarinic antagonist activity. Thus, the compounds of Formula I were tested using the following protocols:

[³H]-N-methylscopolamine ([³H]-NMS) Receptor Binding Using Membranes From Chinese Hamster Ovary (CHO) Cells Selectively Expressing One of the Five Cloned Human Muscarinic Receptors Receptor binding is performed by the methods described by:

1. Buckley N. J., et al., *Mol. Pharmacol.* 1989;35:469–476 "Antagonist binding properties of five cloned muscarinic receptors expressed in CHO-K1 cells" and 2. Dörje F., et al., *J. Pharmacol. Exp. Ther.* 1991;256:727–733 "Antagonist binding profiles of five cloned human muscarinic receptor subtypes" with some modifications as described below.

Following membrane harvest and storage at −80° C., aliquots of membranes (approximately 10–40 μg protein) are added to 2 mL of 10 mM sodium potassium phosphate buffer, pH 7.4, containing 100 pM [$^3$H]-NMS; (78.9 Ci/mmol) and the appropriate test compound. Nonspecific binding is defined as that unaffected by the inclusion of 1 μM atropine. The reaction is initiated by the addition of the membranes and allowed to proceed for 120 minutes at 25° C. with shaking. Termination of the incubation is achieved by rapid vacuum filtration through GF/B Whatman filters using a Brandel Cell Harvester with the filters being washed three times with 5 mL ice-chilled buffer. 10 mL of Beckman Ready Gel scintillation cocktail are added to the filters in vials and the samples are allowed to set overnight before vortexing and counting in a Beckman 800 scintillation counter. IC$_{50}$ values are calculated using a logit equation.

Phosphatidylinositol (PI) Turnover

Phosphatidylinositol turnover assays are performed by the methods described by:

1. Berridge M. J., et al., *Biochem. J.* 1982;206:587–595 "Lithium amplifies agonist-dependent phosphatidylinositol responses in brain and salivary glands" and
2. Berridge M. J., et al., *Nature* 1984;312:315–321 "Inositol triphosphate, a novel second messenger in cellular signal transduction" with some modifications as described below.

CHO Hm1, Hm3, or Hm5 cells are grown at 37° C. with 5% CO$_2$ in Dulbecco's modified Eagle's medium (DMEM) supplemented with 10% fetal bovine serum and 1% nonessential amino acids. Four to 6 days after seeding 12-well plates, the nutrient medium is aspirated and the cells are labelled with 1 μCi/mL of [$^3$H]myoinositol (specific activity=15–18.8.Ci/mmol) in 0.5 mL of media/well. After 48 hours, the medium is aspirated and the cells are washed 2 times with 1 mL MEM containing 10 mM LiCl. 0.5 mLMEM/LiCl then is added to each well and allowed to incubate at 37° C. for at least 15 minutes. The stimulation period is initiated by the addition of 10 μL of the appropriate agonist concentration and allowed to proceed for 15 minutes, at which time the reaction is terminated by the aspiration of medium and the addition of 0.5 mL ice-cold 5% trichloroacetic acid (TCA). For antagonist experiments, the appropriate antagonist is added simultaneously with carbachol (3 μM for m1, 5 μM for m3, and 3 μM for m5). After waiting at least 15 minutes, the TCA extract is applied to Dowex-formate columns (Biorad AG 1-X8 resin, formate form, 100–200 mesh). The wells are rinsed with 0.5 mL distilled H$_2$O and also applied to the columns. The columns are washed 4 times with 3 mL 5 mMmyo-inositol and then total [$^3$H]-inositol phosphates are eluted into vials with two 2 mL washes of 1 mM ammonium formate containing 0.1M formic acid. Beckman Ready Gel scintillation cocktail (10 mL) is added and the samples counted in a Beckman 2800 scintillation counter. The efficacy of agonists is estimated from the maximal effect of the compounds on PI turnover (expressed as a percent of the stimulation produced by carbachol (1 mM)). EC$_{50}$ and IC$_{50}$ values are also calculated for both agonists and antagonists, respectively.

The data in the tables show the muscarinic antagonist activity of representative compounds of Formula I.

TABLE I

| | Biological Activity of Compounds of Formula I | | | | | |
|---|---|---|---|---|---|---|
| Example Number | Compound | IC$_{50}$ (nM) | | | | |
| | | m1 | m2 | m3 | m4 | m5 |
| 1 | 1-Ethyl-1,2,5,6-tetrahydro-4-phenyl-3-pyridine-carboxylic acid, 2-methylpropyl ester | 120.5 | 427.5 | 257.5 | 742.6 | 407.3 |
| 2 | 1-Ethyl-1,2,5,6-tetrahydro-4-phenyl-3-pyridine-carboxylic acid, decyl ester | 106.1 | 20.5 | 399.54 | 566.2 | 235.6 |
| 3 | 1-Ethyl-1,2,5,6-tetrahydro-4-phenyl-3-pyridine-carboxylic acid, phenyl ester | 1820.0 | 954.0 | 4070.0 | 8429.0 | 1569.0 |
| 4 | 1-Ethyl-1,2,5,6-tetrahydro-4-phenyl-3-pyridine-carboxylic acid, 1-methylethyl ester | 480.7 | 347.1 | 765.9 | 642.8 | 1048.4 |
| 5 | 1-Ethyl-1,2,5,6-tetrahydro-4-phenyl-3-pyridine-carboxylic acid, hexyl ester | 35.0 | 227.0 | 349.5 | 367.0 | 138.9 |
| 6 | 1-Ethyl-1,2,5,6-tetrahydro-4-phenyl-3-pyridine-carboxylic acid, 3-cyclohexylpropyl ester | 963.2 | 10943.7 | 24861.7 | 19581.2 | 10969.8 |
| 7 | 1-Ethyl-1,2,5,6-tetrahydro-4-phenyl-3-pyridine-carboxylic acid, 4-phenylbutyl ester | 69.2 | 2162.1 | 1842.0 | 2775.5 | 842.0 |
| 8 | 1-Ethyl-1,2,5,6-tetrahydro-4-phenyl-3-pyridine-carboxylic acid, pentyl ester | 84.8 | 1500.5 | 918.0 | 701.0 | 374.0 |
| 9 | 1-Ethyl-1,2,3,6-tetrahydro-4-phenyl-3-pyridine-carboxylic acid, decyl ester | 484.2 | 1174.8 | 983.0 | 2123.9 | 1114.8 |
| 10 | 1-Ethyl-1,2,3,6-tetrahydro-4-phenyl-3-pyridine-carboxylic acid, phenyl ester | 19039.0 | 14598.0 | 16753.0 | 31125.0 | 31058.0 |
| 11 | 1-Ethyl-1,2,3,6-tetrahydro-4-phenyl-3-pyridine-carboxylic acid, hexyl ester | 27.3 | 2734.2 | 1308.0 | 2030.0 | 508.2 |
| 12 | 1-Ethyl-1,2,3,6-tetrahydro-4-phenyl-3-pyridine-carboxylic acid, 3-cyclohexylpropyl ester | 610.6 | 468.0 | 2801.3 | 1167.2 | 1260.5 |
| 13 | 1-Ethyl-1,2,3,6-tetrahydro-4-phenyl-3-pyridine-carboxylic acid, 4-phenylbutyl ester | 743.1 | 3323.1 | 14309.6 | 7422.0 | 5000.0 |
| 14 | 1-Ethyl-1,2,3,6-tetrahydro-4-phenyl-3-pyridine-carboxylic acid, pentyl ester | 63.7 | 600.7 | 356.9 | 432.4 | 341.9 |
| 15 | 1-Ethyl-1,2,3,6-tetrahydro-4-phenyl-3-pyridine-carboxylic acid, 2-methylpropyl ester | 128.0 | 1248.2 | 844.6 | 896.9 | 558.9 |
| 16 | 1-Ethyl-1,2,3,6-tetrahydro-4-phenyl-3-pyridine-carboxylic acid, 2-(4-chlorophenyl)ethyl ester | 171.9 | 1285.4 | 151.0 | 1847.0 | 558.7 |
| 17 | 1-Ethyl-1,2,3,6-tetrahydro-4-phenyl-3-pyridine-carboxylic acid, 2-(4-methylphenyl)ethyl ester | 93.5 | 956.4 | 1491.0 | 1756.1 | 190.3 |
| 18 | 1-Ethyl-1,2,3,6-tetrahydro-4-phenyl-3-pyridine- | 54.2 | 666.3 | 109.6 | 167.6 | 214.5 |

TABLE I-continued

Biological Activity of Compounds of Formula I

| Example Number | Compound | $IC_{50}$ (nM) | | | | |
|---|---|---|---|---|---|---|
| | | m1 | m2 | m3 | m4 | m5 |
| | carboxylic acid, 1-cyclohexylmethyl ester | | | | | |
| 19 | 1-Ethyl-1,2,5,6-tetrahydro-4-phenyl-3-pyridine-carboxylic acid, 1-cyclohexylmethyl ester | 14.1 | 564.9 | 155.8 | 142.7 | 115.4 |
| A[1] | 1-Ethyl-1,2,5,6-tetrahydro-4-phenyl-3-pyridine-carboxylic acid, cyclohexyl ester | 18.1 | 255.2 | 40.8 | 62.0 | 54.1 |
| B[1] | 1-Ethyl-1,2,5,6-tetrahydro-4-phenyl-3-pyridine-carboxylic acid, 2-phenylethyl ester | 9.6 | 243.6 | 100.7 | 69.7 | 78.1 |
| C[1] | 1-Ethyl-1,2,5,6-tetrahydro-4-phenyl-N,N-dimethyl-3-pyridinecarboxamide | 5007.7 | 12296.1 | 8993.6 | 13481.6 | 6077.3 |
| D[1] | 1-Ethyl-1,2,5,6-tetrahydro-4-phenyl-N-methyl-3-pyridinecarboxamide | 21116.5 | 34811.8 | 38735.8 | 73099.4 | 49098.2 |
| E[1] | 1,4-Dimethyl-1,2,5,6-tetrahydro-3-pyridine-carboxylic acid, methyl ester | 60984.3 | 10436.3 | 67951.0 | >50000 | 73843.3 |
| F[1] | 1-Propyl-1,2,5,6-tetrahydro-4-butyl-3-pyridine-carboxylic acid, methyl ester | 17495.7 | 5337.5 | 14935.2 | 50683.5 | 41232.6 |
| G[1] | 1-Ethyl-1,2,5,6-tetrahydro-4-phenyl-3-pyridine-carboxylic acid, methyl ester | 2308.4 | 1727.9 | 5523.7 | 13691.8 | 977.3 |
| H[1] | 1-Ethyl-1,2,3,6-tetrahydro-4-phenyl-3-pyridine-carboxylic acid, methyl ester | 33117.6 | 28264.5 | 88401.3 | 13042.1 | 16901.9 |

[1] Disclosed in U.S. Pat. No. 4,745,123

TABLE II

Effects of Selected Compounds of Formula I on PI Turnover in CHO Hm1 Cells

| Example Number | Compound | % Basal Control* |
|---|---|---|
| 3 | 1-Ethyl-1,2,5,6-tetrahydro-4-phenyl-3-pyridine-carboxylic acid, phenyl ester | 99 |
| 5 | 1-Ethyl-1,2,5,6-tetrahydro-4-phenyl-3-pyridine-carboxylic acid, hexyl ester | 109 |
| 10 | 1-Ethyl-1,2,3,6-tetrahydro-4-phenyl-3-pyridine-carboxylic acid, phenyl ester | 79 |
| 11 | 1-Ethyl-1,2,3,6-tetrahydro-4-phenyl-3-pyridine-carboxylic acid, hexyl ester | 98 |
| A[1] | 1-Ethyl-1,2,5,6-tetrahydro-4-phenyl-3-pyridine-carboxylic acid, cyclohexyl ester | 108 |
| B[1] | 1-Ethyl-1,2,5,6-tetrahydro-4-phenyl-3-pyridine-carboxylic acid, 2-phenylethyl ester | 90 |
| G[1] | 1-Ethyl-1,2,5,6-tetrahydro-4-phenyl-3-pyridine-carboxylic acid, methyl ester | 89 |
| H[1] | 1-Ethyl-1,2,3,6-tetrahydro-4-phenyl-3-pyridine-carboxylic acid, methyl ester | 108 |

*100 μM of each compound was used. Test run in triplicate.
[1] Disclosed in U.S. Pat. No. 4,745,123

TABLE III

Inhibition of Carbachol Stimulation of PI Turnover in CHO Hm1 Cells By Selected Compounds of Formula I

| Example Number | Compound | % Inhibition |
|---|---|---|
| 3 | 1-Ethyl-1,2,5,6-tetrahydro-4-phenyl-3-pyridinecarboxylic acid, phenyl ester | 100 |
| 5 | 1-Ethyl-1,2,5,6-tetrahydro-4-phenyl-3-pyridinecarboxylic acid, hexyl ester | 99 |
| 11 | 1-Ethyl-1,2,3,6-tetrahydro-4-phenyl-3-pyridinecarboxylic acid, hexyl ester | 100 |
| A[1] | 1-Ethyl-1,2,5,6-tetrahydro-4-phenyl-3-pyridinecarboxylic acid, cyclohexyl ester | 97 |
| B[1] | 1-Ethyl-1,2,5,6-tetrahydro-4-phenyl-3-pyridinecarboxylic acid, 2-phenylethyl ester | 89 |
| G[1] | 1-Ethyl-1,2,5,6-tetrahydro-4-phenyl-3-pyridinecarboxylic acid, methyl ester | 40 |
| H[1] | 1-Ethyl-1,2,3,6-tetrahydro-4-phenyl-3-pyridinecarboxylic acid, methyl ester | 0 |

[1] Disclosed in U.S. Pat. No. 4,745,123

The data in Table I shows that Examples A, B, and 11 have remarkable affinity for m1 receptors, e.g., $IC_{50} = 18.1$, 9.6, and 27.3 nM, respectively. In addition, Examples A and B are also potent at other muscarinic receptor subtypes (Example B, m4 = 69.7 nM, m5 = 78.1 nM; Example A, m3 = 40.8 nM, m4 = 62.0 nM, m5 = 54.1 nM).

None of the selected compounds shown in Tables II and III produced any significant stimulation of phosphatidylinositol (PI) hydrolysis at high concentration (100 μM) in CHO Hm1 cells, indicating that none of them is efficacious as a muscarinic agonist (Table II). However, the blockade of carbachol stimulation of PI turnover produced by some of them in CHO Hm1 cells (Table III) is convincing evidence that the preferred compounds are indeed muscarinic antagonists. For example, the weak binding of Examples G and H (i.e., methyl esters) correlates well with their weak inhibition of carbachol's effects. However, the remaining examples (3, 5, C, B, and 11) are potent antagonists and all examples potently inhibit the effects of the muscarinic agonist, carbachol (89–100%). These data illustrate that the methyl esters (Examples G and H) are not useful muscarinic antagonists and the larger esters (Examples 3, 5, C, B, and 11) are potent muscarinic antagonists. The binding data (Table I) indicate that certain preferred compounds possess remarkable and unexpected selectivity for one or more muscarinic receptor subtypes. For instance, Examples 5, B, and 11 display very high selectivity for m1 receptors. As indicated above, selective blockade of m1 receptors would be useful in reducing gastric acid secretion and in the treatment of gastric ulcers.

Compounds of Formula I are prepared as outlined in Schemes I, II, and III.

SCHEME I

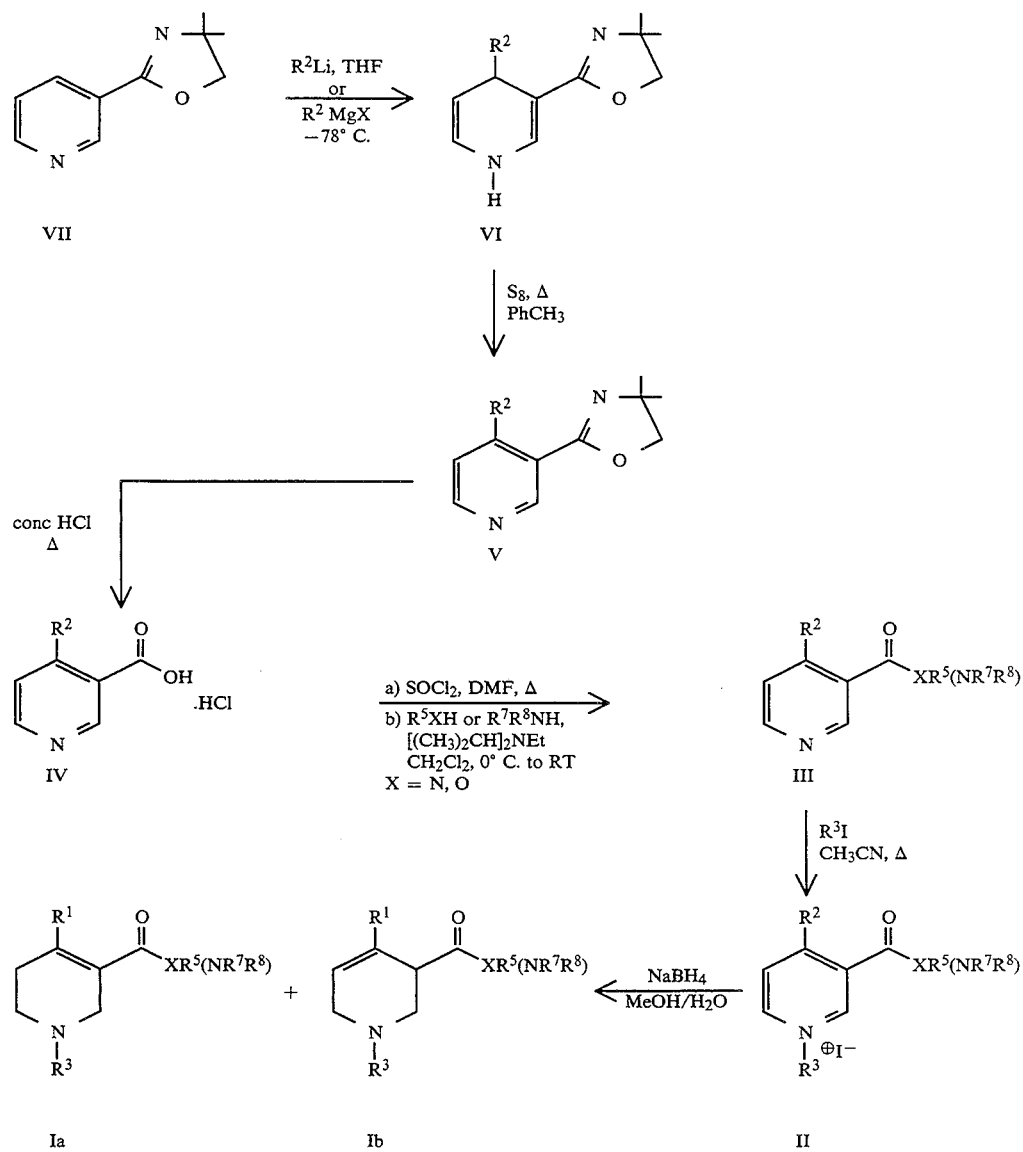

SCHEME II

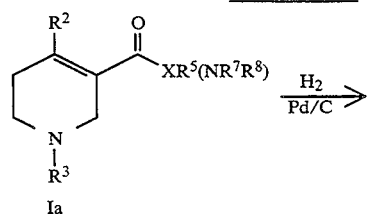

-continued
SCHEME II

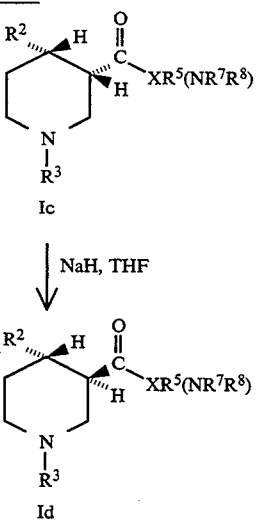

SCHEME III

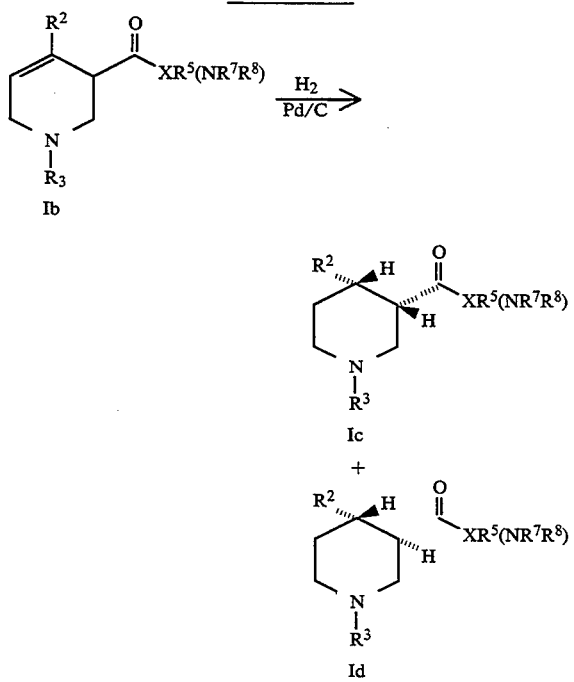

All examples shown in Table I can be prepared by the synthetic route illustrated in Schemes I to III. Reaction of protected nicotinic acid derivatives, e.g., oxazolines of Formula VII, with various organolithium or organomagnesium compounds gives the 4-substituted dihydropyridines of Formula VI. Aromatization of a compound of Formula VI is obtained in the presence of sulfur or other oxidizing agents, such as, for example, DDQ, chlorinal, $MnO_2$ and the like in a solvent such as, for example, toluene and the like to give the 4-substituted pyridine of Formula V. Treatment of a compound of Formula V with acid, such as, for example, concentrated HCl, yields the 4-substituted-3-pyridinecarboxylic acids of Formula IV, versatile intermediates for the synthesis of various esters, thioesters, and amides of 4-substituted-tetrahydro-3-pyridinecarboxylic acids. Esters, thioesters, or amides of Formula III can be synthesized by activating acids of Formula IV with an acid halide, such as, for example, thionyl chloride, and the like. The resulting acid halide can then be treated with various alcohols, mercaptans, or amines in the presence of a base such as, for example, N,N-diisopropylethylamine and the like to give a compound of Formula III. Various quaternary salts of Formula II can be obtained by treating a compound of Formula III with various alkyl halides to give a compound of Formula III. Treatment of a compound of Formula II with a reducing agent such as, for example, sodium borohydride and the like, affords 4-substituted tetrahydropyridines Ia and Ib, which can easily be separated by medium pressure liquid chromatography.

Catalytic hydrogenation of a compound of Formula Ia (Scheme II) yields primarily the cis-piperidine analog of Formula Ic. Separation of the cis-analog from the minor amount of trans compound can be performed by medium pressure liquid chromatography. Equilibration of Ic to the trans analog Id can be performed using sodium hydride or some other base such as potassium hydride, sodium ethoxide, and the like. Catalytic hydrogenation of Ib (Scheme III) yields a mixture of cis (Ic) and trans (Id) 4-substituted tetrahydropyridines. Separation of Ic and Id via medium pressure liquid chromatography yields pure cis and pure trans analogs.

Resolution of enantiomers of the various tetrahydropyridine and piperidine analogs of Formula I can be performed using conventional methodology such as, for example, by formation of chiral acid adducts followed by several recrystallizations.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70 percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient-sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as muscarinic antagonists, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

1-Ethyl-1,2,5,6-tetrahydro-4-phenyl-3-pyridinecarboxylic acid, 2-methylpropyl ester, oxalate (1:1) and 1-Ethyl-1,2,3,6-tetrahydro-4-phenyl-3-pyridinecarboxylic acid, 2-methylpropyl ester, oxalate (1:1)

To a cooled ($-78°$ C.) solution of 3-(4,5-dihydro-4,4-dimethyl-2-oxazolyl)pyridine [Hauck A. E., et al., *J. Chem. Soc. Perkin I* 1980:2070–2076] (140.0 g, 0.79 mol) in 500 mL dry tetrahydrofuran (THF), phenyllithium (1.42 mol, 1.8 eq) is added under a nitrogen atmosphere until gas chromatography (GC) analysis indicates no more starting material is present. The reaction mixture is stirred for 10 minutes and then quenched with 500 mL water at $-78°$ C. After warming the reaction mixture to room temperature with a water bath, 700 mL of diethyl ether is added to the mixture. The resulting solid is filtered, rinsed once with chilled methanol, and then dried at 40° C. in a vacuum oven overnight to yield 166.6 g (0.65 mol) of 1,4-dihydro-3-(4,5-dihydro-4,4-dimethyl-2-oxazolyl)-4-phenylpyridine.

The dihydropyridine obtained above (80.6 g, 0.31 mol) and sulfur (10.6 g, 0.33 mol, 1.04 eq) are refluxed in 750 mL of toluene until GC analysis indicates that the reaction is complete (about 3.5 hours). The mixture is cooled to room temperature and filtered. The mother liquor is concentrated in vacuo and then kept under vacuum overnight. The crude material is distilled yielding 65.3 g (0.25 mol) of the desired 3-(4,5-dihydro-4,4-dimethyl-2-oxazolyl)-4-phenylpyridine (bp 163°–166° C. at 2.8–3.2 mm Hg).

The oxazoline obtained above (108 g, 0.42 mol) and 220 mL concentrated hydrochloric acid (HCl) are refluxed for 16 hours. The mixture is cooled to room temperature, filtered, and rinsed with 300 mL 1N HCl. The white solid is dried in a vacuum oven at 40° C. for 6 hours to give 95.0 g (0.40 mol) of the desired 4-phenyl-3-pyridinecarboxylic acid, mp 245°–246° C. A solution of the acid (10.0 g, 0.042 mol) and 5 mL dimethylformamide (DMF) in 100 mL of thionyl chloride are refluxed for 24 hours under a nitrogen atmosphere. The mixture is cooled to room temperature and concentrated in vacuo to give the corresponding acid chloride. To a cooled (0° C.) solution of 2-methyl-1-propanol (3.42 g, 0.046 mol) and N,N-diisopropylethyl amine (3.01 g, 0.046 mol) in 100 mL methylene chloride, the crude acid chloride in 50 mL methylene chloride is added dropwise. The mixture is allowed to gradually warm to room temperature and stirred for 16 hours under a nitrogen atmosphere. The reaction mixture is diluted with 100 mL saturated aqueous solution of sodium bicarbonate (NaHCO$_3$) and extracted twice with methylene chloride. The combined organic layers are washed with water, dried (MgSO$_4$) and concentrated in vacuo to give the crude product. Purification by medium pressure liquid chromatography (silica gel, 25% ethyl acetate (EtOAc)/hexane) affords 9.80 g (0.038 mol) of the desired 2-methylpropyl 4-phenyl-3-pyridinecarboxylate.

A solution of this ester (4.0 g, 0.0156 mol) and ethyl iodide (16.12 g, 0.1034 mol) in 150 mL acetonitrile is refluxed for 24 hours under nitrogen. The reaction mixture is cooled to room temperature and concentrated in vacuo to afford 6.42 g (0.011 mol) of the quaternary ethyl iodide salt. To a cooled (0° C.) turbid solution of the salt (6.42 g) in 60 mL methanol/water (MeOH/H$_2$O) (1:1), sodium borohydride (1.2 g, 0.03 mol) is added portionwise. The foaming mixture is allowed to stir at 0° C. for 30 minutes. The mixture is concentrated in vacuo to one-half the original volume, acidified to pH 1 with 15 mL concentrated HCl, then basified to pH 11 using 15 mL of ammonium hydroxide. The mixture is then extracted twice with EtOAc, dried (Na$_2$SO$_4$), and concentrated in vacuo to give a mixture of the 1,2,5,6- and 1,2,3,6-tetrahydropyridines. The isomers are separated by medium pressure liquid chromatography (silica, 40% EtOAc/hexane) to give 1-ethyl-1,2,5,6-tetrahydro-4-phenyl-3-pyridinecarboxylic acid, 2-methylpropyl ester (0.87 g) and 1-ethyl-1,2,3,6-tetrahydro-4-phenyl-3-pyridinecarboxylic acid, 2-methylpropyl ester (0.23 g). To a solution of the 1,2,5,6-tetrahydropyridine (0.80 g, 0.002 mol) in 50 mL diethyl ether, oxalic acid (0.25 g, 0.002 mol) in 10 mL diethyl ether is added dropwise. After stirring at room temperature for 16 hours, the white solid is filtered, rinsed with diethyl ether, and air-dried to give 0.88 g (0.002 mol) of the 1,2,5,6 isomer; mp 140°–142° C. To a solution of the 1,2,3,6-tetrahydropyridine (0.20 g, 0.0006 mol) in 15 mL of diethyl ether, oxalic acid (0.06 g, 0.0006 mol) in 4 mL of diethyl ether is added dropwise. After stirring at room temperature for 16 hours, the solid is filtered, rinsed with diethyl ether, and air-dried to give 0.10 g (0.002 mol) of the 1,2,3,6 isomer; Mass Spectroscopy (MS)(CI+): 288 (MH+).

In a process analogous to Example 1 using appropriate starting materials, the corresponding compounds of Formula I are prepared as follows.

EXAMPLE 2

1-Ethyl-1,2,5,6-tetrahydro-4-phenyl-3-pyridinecarboxylic acid, decyl ester

The title compound is obtained as an oil from 4-phenyl-3-pyridinecarboxylic acid (5.0 g, 0.021 mol) and decyl alcohol (3.6 g, 0.023 mol); MS(CI+): 372 (MH+), 371 (M+).

EXAMPLE 3

1-Ethyl-1,2,5,6-tetrahydro-4-phenyl-3-pyridinecarboxylic acid, phenyl ester, oxalate (1:1) salt The title compound, mp 185°–188° C., is prepared from 4-phenyl-3-pyridinecarboxylic acid (5.0 g, 0.021 mol) and phenol (2.2 g, 0.023 mol).

EXAMPLE 4

1-Ethyl-1,2,5,6-tetrahydro-4-phenyl-3-pyridinecarboxylic acid, 1-methylethyl ester, oxalate (1:1) salt The title compound, mp 154°–156° C., is prepared from 4-phenyl-3-pyridinecarboxylic acid (5.0 g, 0.02 mol) and isopropyl alcohol (1.4 g, 0.023 mol).

EXAMPLE 5

1-Ethyl-1,2,5,6-tetrahydro-4-phenyl-3-pyridinecarboxylic acid, hexyl ester, oxalate (1:1) salt The title compound, mp 59°–61° C., is prepared from 4-phenyl-3-pyridinecarboxylic acid (10.0 g, 0.042 mol) and hexyl alcohol (4.72 g, 0.046 mol).

EXAMPLE 6

1-Ethyl-1,2,5,6-tetrahydro-4-phenyl-3-pyridinecarboxylic acid, 3-cyclohexylpropyl ester, oxalate (1:1) salt The title compound, mp 139°–141° C., is prepared from 4-phenyl-3-pyridinecarboxylic acid (5.0 g, 0.021 mol) and 3-cyclohexyl-1-propanol (3.3 g, 0.023 mol).

EXAMPLE 7

1-Ethyl-1,2,5,6-tetrahydro-4-phenyl-3-pyridinecarboxylic acid, 4-phenylbutyl ester, oxalate (1:1) salt The title compound, mp 116°–118° C., is prepared from 4-phenyl-3-pyridinecarboxylic acid (5.0 g, 0.021 mol) and 4-phenyl-1-butanol (3.50 g, 0.023 mol).

EXAMPLE 8

1-Ethyl-1,2,5,6-tetrahydro-4-phenyl-3-pyridinecarboxylic acid, pentyl ester, oxalate (1:1) salt The title compound, mp 110°–112° C., is prepared from 4-phenyl-3-pyridinecarboxylic acid (20 g, 0.084 mol) and pentyl alcohol (4.1 g, 0.046 mol).

EXAMPLE 9

1-Ethyl-1,2,3,6-tetrahydro-4-phenyl-3-pyridinecarboxylic acid, decyl ester

The title compound is obtained as an oil from 4-phenyl-3-pyridinecarboxylic acid (5.0 g, 0.021 mol) and decyl alcohol (3.6 g, 0.023 mol); MS(CI+): 372 (MH+), 371 (M+).

EXAMPLE 10

1-Ethyl-1,2,3,6-tetrahydro-4-phenyl-3-pyridinecarboxylic acid, phenyl ester, oxalate (1:1) salt The title compound, mp 127°–130° C., is prepared from 4-phenyl-3-pyridinecarboxylic acid (5.0 g, 0.02 mol) and phenol (2.2 g, 0.023 mol).

EXAMPLE 11

1-Ethyl-1,2,3,6-tetrahydro-4-phenyl-3-pyridinecarboxylic acid, hexyl ester, oxalate (1:1) salt The title compound, mp 122°–124° C., is prepared from 4-phenyl-3-pyridinecarboxylic acid (10.0 g, 0.042 mol) and hexyl alcohol (4.72 g, 0.046 mol).

EXAMPLE 12

1-Ethyl-1,2,3,6-tetrahydro-4-phenyl-3-pyridinecarboxylic acid, 3-cyclohexylpropyl ester, oxalate (1:1) salt The title compound, mp 85°–88° C., is prepared from 4-phenyl-3-pyridinecarboxylic acid (5.0 g, 0.021 mol) and 3-cyclohexylpropanol (3.3 g, 0.023 mol).

EXAMPLE 13

1-Ethyl-1,2,3,6-tetrahydro-4-phenyl-3-pyridinecarboxylic acid, 4-phenylbutyl ester, oxalate (1:1) salt The title compound is obtained as an oil from 4-phenyl-3-pyridinecarboxylic acid (5.0 g, 0.021 mol) and 4-phenylbutanol (3.50 g, 0.023 mol); MS(CI+): 364 (MH+), 363 (M+).

EXAMPLE 14

1-Ethyl-1,2,3,6-tetrahydro-4-phenyl-3-pyridinecarboxylic acid, pentyl ester, oxalate (1:1) salt The title compound, mp 130°–132° C. is prepared from 4-phenyl-3-pyridinecarboxylic acid (20 g, 0.084 mol) and pentyl alcohol (4.1 g, 0.046 mol).

EXAMPLE 15

1-Ethyl-1,2,3,6-tetrahydro-4-phenyl-3-pyridinecarboxylic acid, 2-methylpropyl ester, oxalate (1:1) salt The title compound is obtained as an oil from 4-phenyl-3-pyridinecarboxylic acid (10.0 g, 0.042 mol) and 2-methyl-1-propanol (3.42 g, 0.046 mol); MS(CI+): 288 (MH+), 287 (M+).

EXAMPLE 16

1-Ethyl-1,2,3,6-tetrahydro-4-phenyl-3-pyridinecarboxylic acid, 2-(4-chlorophenyl)ethyl ester, oxalate (1:1) salt The title compound, mp 111°–114° C., is prepared from 4-phenyl-3-pyridinecarboxylic acid (6.50 g, 0.0276 mol) and 4-chlorophenyl-ethyl alcohol (4.75 g, 0.030 mol).

EXAMPLE 17

1-Ethyl-1,2,3,6-tetrahydro-4-phenyl-3-pyridinecarboxylic acid, 2-(4-methylphenyl)ethyl ester, oxalate (1:1) salt The title compound, mp 100°–103° C., is prepared from 4-phenyl-3-pyridinecarboxylic acid (6.50 g, 0.0276 mol) and 4-methylphenylethyl alcohol (4.13 g, 0.030 mol).

EXAMPLE 18

1-Ethyl-1,2,3,6-tetrahydro-4-phenyl-3-pyridinecarboxylic acid, 1-cyclohexylmethyl ester, oxalate (1:1) salt The title compound, mp 110°–112° C., is prepared from 4-phenyl-3-pyridinecarboxylic acid (4.14 g, 0.020 mol) and 1-cyclohexylmethyl alcohol (2.6 g, 0.023 mol).

EXAMPLE 19

1-Ethyl-1,2,5,6-tetrahydro-4-phenyl-3-pyridinecarboxylic acid, 1-cyclohexylmethyl ester The title compound, mp 94°–97° C., is prepared from 4-phenyl-3-pyridinecarboxylic acid (4.14 g, 0.020 mol) and 1-cyclohexylmethyl alcohol (2.6 g, 0.0231 mol).

We claim:

1. A compound selected from the group consisting of:
1-Ethyl-1,2,5,6-tetrahydro-4-phenyl-3-pyridinecarboxylic acid, 3-cyclohexylpropyl ester;
1-Ethyl-1,2,3,6-tetrahydro-4-phenyl-3-pyridinecarboxylic acid, 3-cyclohexylpropyl ester;
1-Ethyl-1,2,5,6-tetrahydro-4-phenyl-3-pyridinecarboxylic acid, 2-cyclohexylethyl ester;
1-Ethyl-1,2,3,6-tetrahydro-4-phenyl-3-pyridinecarboxylic acid, 2-cyclohexylethyl ester;
1-Ethyl-1,2,5,6-tetrahydro-4-phenyl-3-pyridinecarboxylic acid, 2,2-diphenylethyl ester;
1-Ethyl-1,2,3,6-tetrahydro-4-phenyl-3-pyridinecarboxylic acid, 2,2-diphenylethyl ester;
1-Ethyl-1,2,5,6-tetrahydro-4-phenyl-3-pyridinecarboxylic acid, cyclohexylmethyl ester;
1-Ethyl-1,2,3,6-tetrahydro-4-phenyl-3-pyridinecarboxylic, cyclohexylmethyl ester;
1-Ethyl-1,2,5,6-tetrahydro-4-phenyl-3-pyridinecarboxylic acid, 1-naphthyl ester;
1-Ethyl-1,2,3,6-tetrahydro-4-phenyl-3-pyridinecarboxylic, 1-naphthyl ester;
1-Ethyl-1,2,5,6-tetrahydro-4-phenyl-3-pyridinecarboxylic acid, diphenylmethyl ester;
1-Ethyl-1,1,3,6-tetrahydro-4-phenyl-3-pyridinecarboxylic, diphenylmethyl ester;
1-Ethyl-1,2,5,6-tetrahydro-4-phenyl-3-pyridinecarboxylic acid, 2,3-dihydro-1H-inden-1-yl ester;
1-Ethyl-1,2,3,6-tetrahydro-4-phenyl-3-pyridinecarboxylic acid, 2,3-dihydro-1H-inden-1-yl ester;
1-Ethyl-1,2,5,6-tetrahydro-4-phenyl-3-pyridinecarboxylic acid, 1,2,3,4-tetrahydro-1-naphthalenyl ester;
1-Ethyl-1,2,3,6-tetrahydro-4-phenyl-3-pyridinecarboxylic acid, 1,2,3,4-tetrahydro-1-naphthalenyl ester;
1-Ethyl-1,2,5,6-tetrahydro-4-phenyl-3-pyridinecarboxylic acid, 3,3-diphenylpropyl ester;
1-Ethyl-1,2,3,6-tetrahydro-4-phenyl-3-pyridinecarboxylic acid, 3,3-diphenylpropyl ester;
1-Ethyl-1,2,5,6-tetrahydro-4-phenyl-3-pyridinecarboxylic acid, (tetrahydro-2-furanyl)methyl ester;
1-Ethyl-1,2,3,6-tetrahydro-4-phenyl-3-pyridinecarboxylic acid, (tetrahydro-2-furanyl)methyl ester;
1-Ethyl-1,2,5,6-tetrahydro-4-cyclohexyl-3-pyridinecarboxylic acid, 2-cyclohexylethyl ester;
1-Ethyl-1,2,3,6-tetrahydro-4-cyclohexyl-3-pyridinecarboxylic acid, 2-cyclohexylethyl ester;
1-Ethyl-1,2,5,6-tetrahydro-4-cyclohexyl-3-pyridinecarboxylic acid, 2,2-diphenylethyl ester; and
1-Ethyl-1,2,3,6-tetrahydro-4-cyclohexyl-3-pyridinecarboxylic acid, 2,2-diphenylethyl ester.

2. A method of inhibiting gastric acid release; treating bradycardia; treating bronchoconstriction; treating urinary incontinence; treating atonic conditions of the gut and bladder; treating Parkinson's disease; treating dystonias comprising administering to a host suffering therefrom a therapeutic effective amount of a compound of Formula I

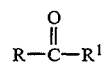

wherein
R is:

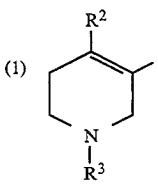

wherein
$R^2$ is
alkyl of from 1 to 6 carbon atoms,
alkenyl of from 2 to 10 carbon atoms,
cycloalkyl of from 3 to 8 carbon atoms,
aryl,
aryl substituted by halogen, hydroxy, nitro, amino,

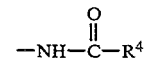

wherein
$R^4$ is
alkyl of from 1 to 4 carbon atoms,
alkyl of from 1 to 4 carbon atoms, or
alkyloxy of from 1 to 4 carbon atoms, or
arylalkyl wherein the alkyl portion is from 1 to 3 carbon atoms and the aryl ring may be unsubstituted or substituted by halogen, hydroxy, nitro, amino,

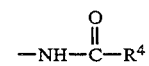

wherein
$R^4$ is
alkyl of from 1 to 4 carbon atoms,
alkyl of from 1 to 4 carbon atoms, or alkyloxy of from 1 to 4 carbon atoms,
heteroaryl, or
heteroaryl substituted by halogen, hydroxy, nitro, amino,

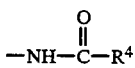

wherein
R⁴ is
  alkyl of from 1 to 4 carbon atoms,
  alkyl of from 1 to 4 carbon atoms, or
  alkyloxy of from 1 to 4 carbon atoms, and
R³ is alkyl of from 1 to 3 carbon atoms, (2) 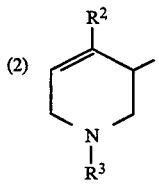

wherein
R² and R³ are as defined above, or (3) 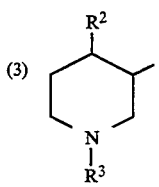

wherein
R² and R³ are as defined above;
R¹ is —XR⁵ wherein R⁵ is
  alkyl of from 3 to 10 carbon atoms,
  alkenyl of from 2 to 10 carbon atoms,
  alkynyl of from 2 to 10 carbon atoms,
  cycloalkyl of from 3 to 8 carbon atoms,
  cycloalkylalkyl wherein alkyl is from 1 to 10 carbon atoms and cycloalkyl is as defined above,
  aryl,
  aryl substituted by halogen, hydroxy, nitro, amino,

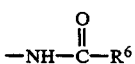

wherein
R⁶ is
  alkyl of from 1 to 4 carbon atoms,
  alkyl of from 1 to 4 carbon atoms, or
  alkyloxy of from 1 to 4 carbon atoms,
  arylalkyl wherein alkyl is from 1 to 10 carbon atoms and the aryl ring may be unsubstituted or substituted by halogen, hydroxy, nitro, amino,

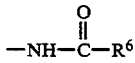

wherein
R⁶ is as defined above,
  alkyl of from 1 to 4 carbon atoms, or alkyloxy of from 1 to 4 carbon atoms,
diarylalkyl wherein alkyl is from 1 to 10 carbon atoms, and the aryl ring is unsubstituted or substituted as defined above,
arylalkenyl wherein alkenyl is from 2 to 10 carbon atoms and the aryl ring is unsubstituted or substituted as defined above,
arylalkynyl wherein alkynyl is from 2 to 10 carbon atoms and the aryl ring is unsubstituted or substituted as defined above,

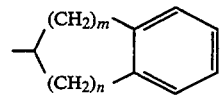

wherein
m and n are each independently zero or an integer of 1 to 3, or

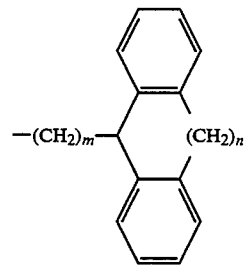

wherein
m and n are as defined above; and
X is O or S; or a pharmaceutically acceptable salt thereof in unit dosage form.

3. A pharmaceutical composition comprising a therapeutic effective amount of a compound according to claim 1 in admixture with a pharmaceutically acceptable excipient, diluent, or carrier.

4. A pharmaceutical composition adapted for administration as an agent for inhibiting gastric acid release; as an agent for treating bradycardia; as an agent for treating broncho-constriction; as an agent for treating urinary incontinence; as an agent for treating atonic conditions of the gut and bladder; as an agent for treating Parkinson's disease; or as an agent for treating dystonias comprising a therapeutically effective amount of a compound according to claim 1 in admixture with a pharmaceutically acceptable excipient, diluent, or carrier.

5. A compound according to claim 2 selected from the group consisting of:
1-Ethyl-1,2,5,6-tetrahydro-4-cyclohexyl-3-pyridinecarboxylic acid, 4-phenylbutyl ester;
1-Ethyl-1,2,3,6-tetrahydro-4-cyclohexyl-3-pyridinecarboxylic acid, 4-phenylbutyl ester;
1-Ethyl-1,2,5,6-tetrahydro-4-cyclohexyl-3-pyridinecarboxylic acid, hexyl ester;
1-Ethyl-1,2,3,6-tetrahydro-4-cyclohexyl-3-pyridinecarboxylic acid, hexyl ester;
1-Ethyl-1,2,5,6-tetrahydro-4-cyclohexyl-3-pyridinecarboxylic acid, 2-phenylethyl ester;
1-Ethyl-1,2,3,6-tetrahydro-4-cyclohexyl-3-pyridinecarboxylic acid, 2-phenylethyl ester;
1-Ethyl-1,2,5,6-tetrahydro-4-cyclohexyl-3-pyridinecarboxylic acid, cyclohexyl ester;

1-Ethyl-1,2,3,6-tetrahydro-4-cyclohexyl-3-pyridinecarboxylic acid, cyclohexyl ester;

1-Ethyl-1,2,5,6-tetrahydro-4-cyclohexyl-3-pyridinecarboxylic acid, n-octyl ester;

1-Ethyl-1,2,5,6-tetrahydro-4-cyclohexyl-3-pyridinecarboxylic acid, n-nonyl ester;

1-Ethyl-1,2,3,6-tetrahydro-4-cyclohexyl-3-pyridinecarboxylic acid, n-heptyl ester;

1-Ethyl-1,2,3,6-tetrahydro-4-cyclohexyl-3-pyridinecarboxylic acid, n-octyl ester; and 1-Ethyl-1,2,3,6-tetrahydro-4-cyclohexyl-3-pyridinecarboxylic acid, n-nonyl ester.

* * * * *